United States Patent
Chancellor et al.

(10) Patent No.: US 7,387,015 B2
(45) Date of Patent: Jun. 17, 2008

(54) MATERIAL STRENGTH INDEXING SYSTEM

(75) Inventors: David M. Chancellor, Dewey, OK (US); Gangerico G. Ramos, Bartlesville, OK (US); Milton B. Enderlin, Houston, TX (US)

(73) Assignee: ConocoPhillips Company, Houston, TX (US)

( * ) Notice: Subject to any disclaimer, the term of this patent is extended or adjusted under 35 U.S.C. 154(b) by 166 days.

(21) Appl. No.: 11/230,716

(22) Filed: Sep. 20, 2005

(65) Prior Publication Data

US 2007/0062263 A1  Mar. 22, 2007

(51) Int. Cl.
 *G01N 3/00*  (2006.01)
(52) U.S. Cl. ............................................................ 73/85
(58) Field of Classification Search ............... 73/81–83, 73/85, 78
 See application file for complete search history.

(56) References Cited

U.S. PATENT DOCUMENTS

| | | | | |
|---|---|---|---|---|
| 2,138,411 A | * | 11/1938 | Tornebohm | 73/81 |
| 2,279,264 A | * | 4/1942 | Hoffman | 73/78 |
| 2,436,435 A | * | 2/1948 | Kent | 73/85 |
| 2,491,667 A | * | 12/1949 | Kent | 73/81 |
| 3,282,094 A | * | 11/1966 | Hinden | 73/150 R |
| 3,289,458 A | * | 12/1966 | Diechert et al. | 73/7 |
| 3,296,857 A | * | 1/1967 | Kaczeus | 73/159 |
| 3,389,463 A | * | 6/1968 | Gerek et al. | 30/164.9 |
| 3,628,736 A | * | 12/1971 | Dega et al. | 73/79 |
| 3,822,588 A | * | 7/1974 | Knight et al. | 73/81 |
| 3,937,069 A | * | 2/1976 | Saunders | 73/81 |
| 4,463,600 A | * | 8/1984 | Hobbs et al. | 73/81 |
| 4,535,623 A | * | 8/1985 | Gilberto | 73/81 |
| 4,820,051 A | * | 4/1989 | Yanagisawa et al. | 356/626 |
| 5,063,785 A | | 11/1991 | Labuz et al. | 73/821 |
| 5,357,786 A | * | 10/1994 | Lung et al. | 73/81 |
| 5,535,627 A | * | 7/1996 | Swanson et al. | 73/597 |
| 5,546,797 A | * | 8/1996 | Dutta et al. | 73/150 A |
| 5,670,711 A | | 9/1997 | Detournay et al. | 73/84 |
| 6,349,595 B1 | | 2/2002 | Civolani et al. | 73/152.02 |
| 6,520,004 B1 | * | 2/2003 | Lin | 73/81 |
| 6,560,550 B2 | | 5/2003 | Omar | 702/42 |

FOREIGN PATENT DOCUMENTS

| | | | |
|---|---|---|---|
| FR | 2558594 A1 | * | 7/1985 |
| JP | 63015139 A | * | 1/1988 |
| JP | 01088336 A | * | 4/1989 |

* cited by examiner

*Primary Examiner*—Hezron E. Williams
*Assistant Examiner*—John Fitzgerald
(74) *Attorney, Agent, or Firm*—Ryan N. Cross; Kameron D. Kelly

(57) ABSTRACT

Apparatus and methods for estimating a physical property of a specimen, particularly the specimen strength, are provided. More specifically, a roller indenter comprising an indenting wheel and a force indicator is used to create an elongated trough in a specimen. The width of the trough is measured as a plurality of locations and correlated with a known standard to provide an estimate of the strength of the sample.

32 Claims, 5 Drawing Sheets

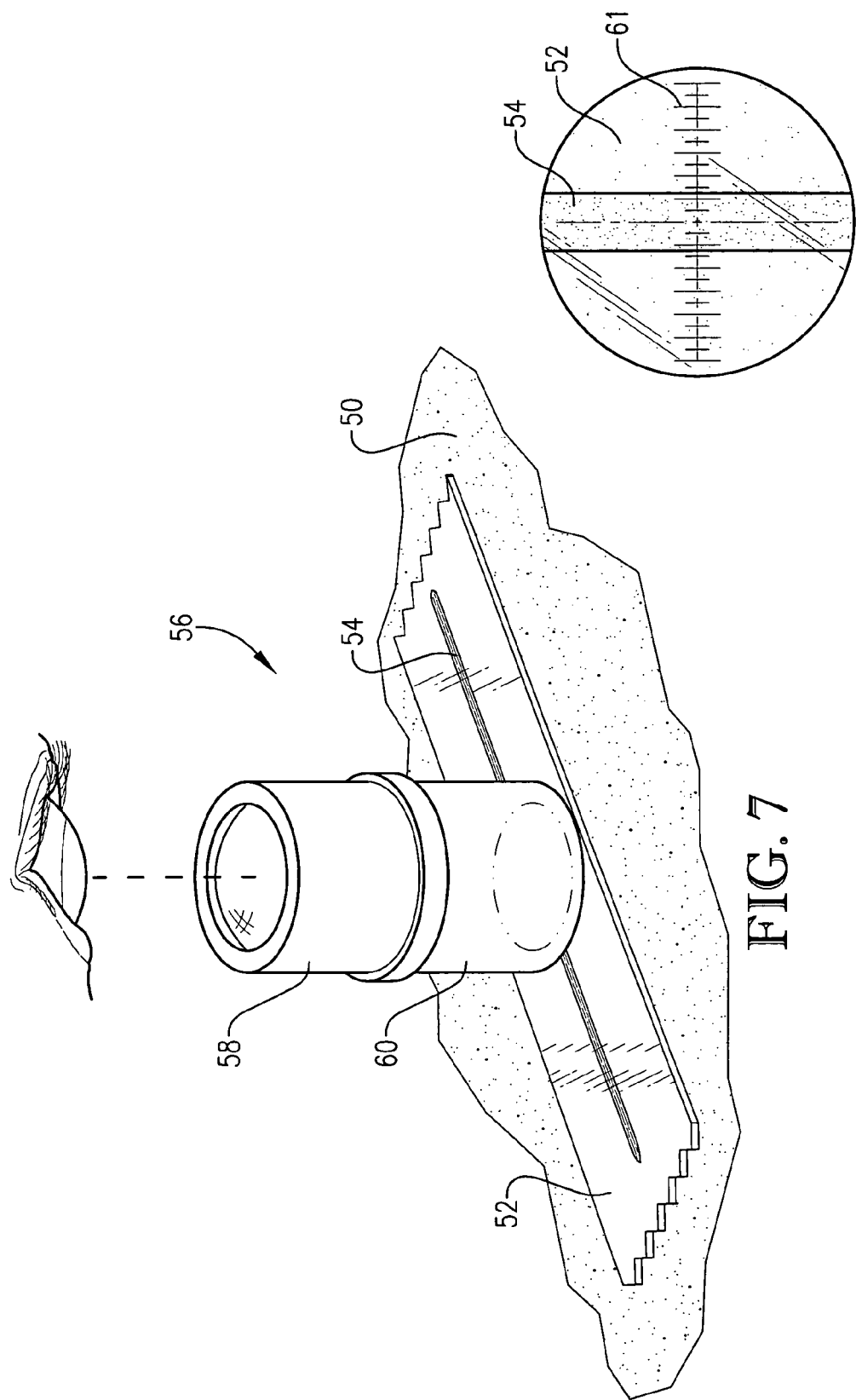

MATERIAL STRENGTH INDEXING SYSTEM

BACKGROUND OF THE INVENTION

1. Field of the Invention

The present invention relates generally to apparatus and methods for non-destructively measuring the strength of a specimen, especially a rock specimen from a subterranean formation. More particularly, the present invention is directed toward a light-weight, portable device that directly measures rock strength without destroying the entire rock specimen.

2. Description of the Prior Art

Geologists, geophysicists, and engineers often need to quantitatively measure the strength of rocks making up a particular subterranean rock formation during activities such as well drilling and well completion. The rock strength will frequently dictate whether a well bore needs to be cased or whether the rock formation possesses the strength to avoid collapse.

Various methods exist for determining the strength of a rock specimen. However, these methods generally involve sending the specimen to a remote laboratory for testing. In the meanwhile, the professionals working in the field may have to cease or slow down operations until the testing is completed. Also, many conventional methods for determining rock strength involve applying shear and normal forces to the specimen to the point of specimen failure. As such methods result in the destruction of the specimen, there is no way to perform repeat testing on the same specimen.

Therefore, there exists a need for a portable device that can be used in the field to measure the strength of a rock specimen without destroying the specimen in case further testing is required.

OBJECTS AND SUMMARY OF THE INVENTION

It is, therefore, an object of the present invention to provide a method for testing the strength of a specimen, particularly a rock specimen, while avoiding the use of destructive shear forces. It is a further object of the present invention to provide means for estimating the strength of a rock specimen without having to send the specimen to a laboratory for analysis so a to provide an immediate indication of the nature of a particular subterranean formation.

It should be understood that the above-listed objects are only exemplary, and not all the objects listed above need be accomplished by the invention described and claimed herein.

Accordingly, in one embodiment of the present invention there is provided a method for testing the strength of a specimen, the method comprising: (a) using a roller indenter to create an elongated trough in at least one specimen; and (b) measuring the size of the trough at a plurality of locations.

In another embodiment of the present invention there is provided a method for testing a specimen, the method comprising: (a) scoring at least one specimen with a roller indenter to create an elongated trough in the at least one specimen, the roller indenter comprising a force indicator and an indenting wheel coupled to the force indicator; (b) measuring the size of the trough at a plurality of locations; and (c) correlating the size measurements with at least one known standard to estimate a property of the specimen.

In yet another embodiment of the present invention there is provided a roller indenter for testing the strength of a rock specimen, the indenter comprising: a force indicator; and an indenting wheel rotatably coupled to the force indicator, the indenting wheel presenting a sharpened circumferential edge.

BRIEF DESCRIPTION OF THE DRAWING FIGURES

A preferred embodiment of the present invention is described in detail below with reference to the attached drawing figures, wherein:

FIG. 7 is a view depicting an optical reader placed over a portion of the trough thereby enabling measurement of the width of the trough; and FIG. 8 is a view looking through the optical reader shown in FIG. 7, the optical reader containing a series of graduated marks used for determining the width of the trough.

DETAILED DESCRIPTION OF THE PREFERRED EMBODIMENT

When performing various subterranean operations, such as well formation and completion, it is important to identify and understand the properties of the specific subterranean formations involved. Sending rock specimens from the field to the laboratory for analysis can be very time consuming, particularly when the operation is being performed in a remote location. The present invention provides apparatus and methods for estimating the strength (i.e., hardness and compressibility) of a specimen in an efficient manner thereby eliminating the need to send every specimen to a laboratory for testing. Often times, only in those instances where the estimated rock strength is close to the project tolerance limits will further lab testing be required.

Figure 1:
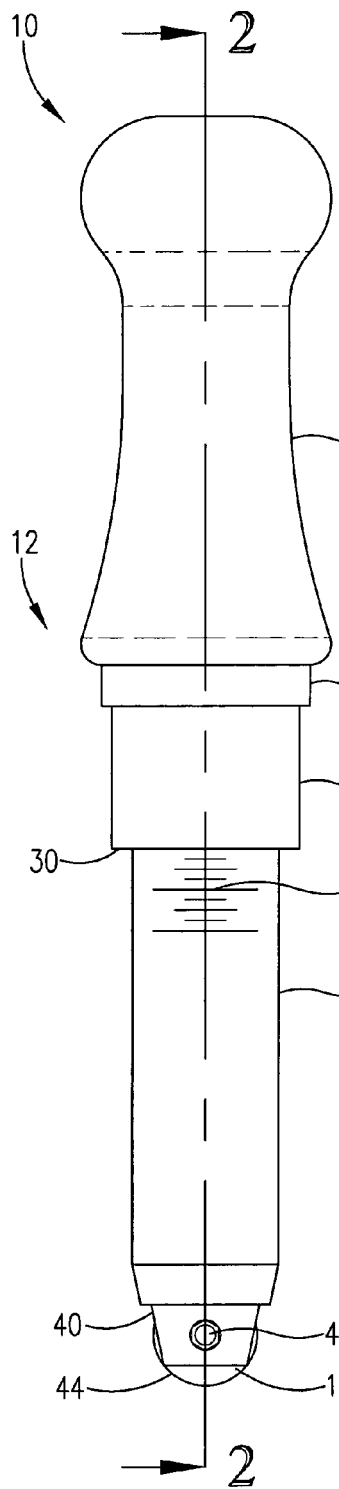
FIG. 1 is an elevational view of a roller indenter constructed in accordance with the present invention.

Referring initially to FIG. 1, a preferred roller indenter 10 according to the present invention is shown. Roller indenter 10 comprises a hand-held force indicator section 12 coupled to an indenting wheel 14 which is configured to contact a rock specimen to create an elongated trough thereon. The operation of roller indenter 10 is described below in further detail.

Force indicator section 12 comprises a handle 16 that is threadably coupled to a handle adaptor 18. Handle 16 preferably presents an ergonomic shape so as to be easily grasped by the hand of a user. Adaptor 18 includes a central annular orifice through which a central pin 20 (FIG. 2) is slidably received. Pin 20 comprises upper and lower portions 22 and 24, respectively. Upper portion 22 is generally in the form of an elongated cylindrical section whereas lower portion 24 comprises a generally cylindrical section presenting a diameter that is wider than that of upper portion 22. Lower portion 24 also contains a "U-shaped" groove formed therein. This groove extends longitudinally along one side of lower portion 24, across the bottom wall of lower portion 24, and back up the opposite side of lower portion 24. As explained below, this U-shaped groove accommodates a dye pad 25 which contacts indenter wheel 14 during operation of roller indenter 10. Pin 20 functions as the primary, internal support structure for roller indenter 10.

Adaptor 18 is also threadably coupled to a force indicator sleeve 26 having a sufficient internal diameter to accommodate a hollow, cylindrical casing 28 slidably received therein. Sleeve 26 comprises a circumferential, inwardly extending lip 30 located proximate the lower end thereof. Lip 30 cooperates with a circumferential, outwardly extending lip 32 on casing 28 to maintain sleeve 26 in an overlapping relationship to casing 28.

Figure 2:
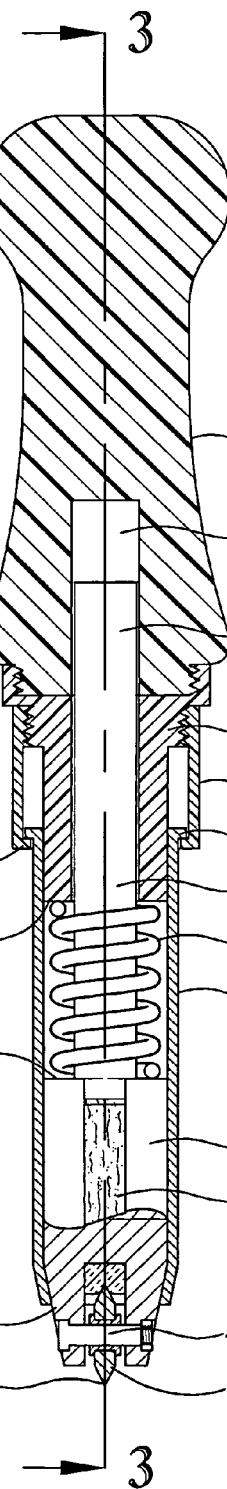
FIG. 2 is a partial elevation and partial cross-sectional view of the roller indenter of FIG. 1 taken along line 2-2.
Figure 3:
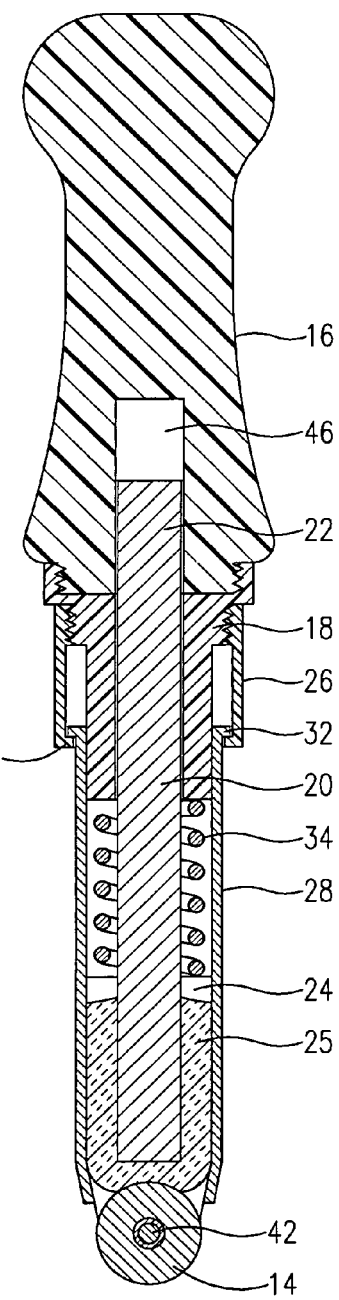
FIG. 3 is a cross-sectional view of the roller indenter of FIG. 2 taken along line 3-3.

A spring 34 is located inside casing 28 and disposed around upper pin portion 22. Preferably, spring 34 is under compression thereby biasing the lower end 36 of handle adaptor 18 away from the top surface 38 of lower pin portion 24. Lip 32 engages the top of lip 30 thereby keeping spring 34 under compression even when roller indenter 10 is at rest as shown in FIGS. 1-3.

The bottom end 40 of lower pin portion 24 is tapered and cooperates with the tapered lower end of casing 28 in order to secure pin 20 inside casing 28. As noted above, lower pin portion 24 contains a groove that not only accommodates dye pad 25, but also at least a portion of indenter wheel 14. Wheel 14 is releasably secured to bottom end 40 by axle 42 such as through a nut and bolt to facilitate replacement of wheel 14 as needed. Wheel 14 comprises a sharpened circumferential edge 44 presenting a taper angle in the range of from about 20 to about 120 degrees, more preferably from about 50 to about 110 degrees, and most preferably from about 80 to about 100 degrees. The taper angle is generally measured as the angle between opposed sides of wheel 14 proximate circumferential edge 44.

Figure 4:
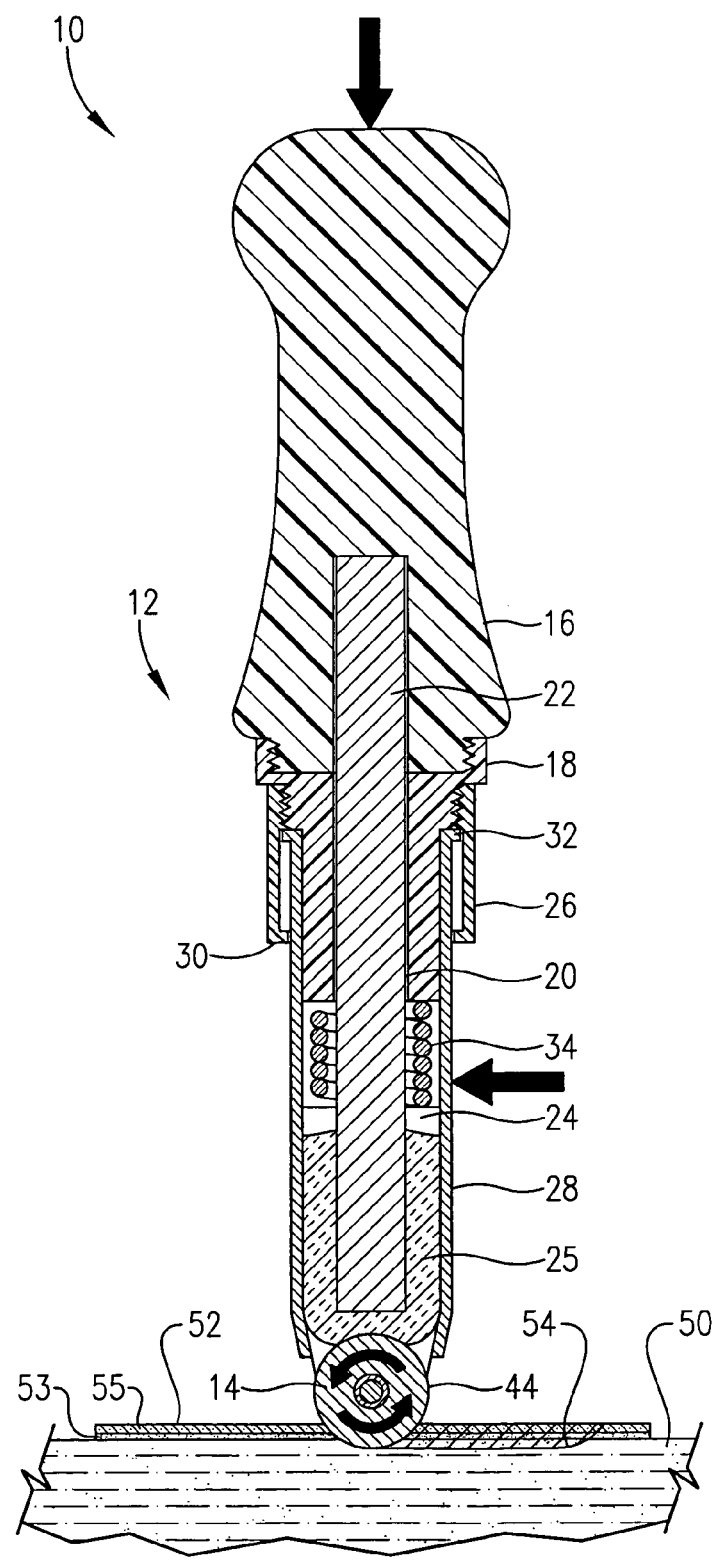
FIG. 4 is a cross-sectional view of the roller indenter being used to create an elongated trough in a rock specimen.

Operation of roller indenter 10 to test the strength of a rock specimen 50 is shown in FIG. 4. Preferably, the rock specimen 50 is prepared by placing a strip of adhesive film 52 on a portion of the specimen outer surface. Film 52 generally includes an adhesive substrate 53 to attach the film to the surface of specimen 50 and a flexible mat layer 55. Film 52 generally presents a thickness of less than about 0.5 inches (12.7 mm), more preferably less than about 0.1 inches (2.54 mm), and most preferably less than about 0.01 inches (0.254 mm). A user, grasping handle 16 places wheel 14 in contact with the specimen and applies a downward force to handle 16 in a direction parallel to the longitudinal axis of indenter 10 and toward the specimen. The downward force causes handle 16 and handle adaptor 18 to slide downwardly along pin 20 thereby compressing spring 34. Handle 16 comprises a slot 46 (FIG. 3) to accommodate upper pin portion 22 as handle 16 and adaptor 18 slide along pin 20. The user can control the magnitude of the force being exerted on the sample using the graduated scale 48 on casing 28. Alternatively, a digital force indicator may be provided. This digital indicator may be electronically coupled to a computer to record or log the forces being applied to the sample. Such digital indicator may be directly coupled with spring 34 to measure the compression thereof. Handle 16 and sleeve 26 maybe shifted downwardly so that sleeve lip 30 lines up with the desired hash mark of scale 48. Preferably, the downward force exerted has a magnitude of from about 0.5 to about 50 pounds, more preferably from about 1 to about 30 pounds, and most preferably from about 1.5 to about 25 pounds.

It is contemplated herein that the manual nature of indenter 10 can be automated so that the indenter need not be hand-held and a constant force applicator used instead of a handle 16 and spring 34 assembly. A constant force applicator, while more complex, has the advantage of more accurately and consistently applying a particular force to the specimen. Such a device may comprise a very portable assembly even though this assembly may not necessarily be hand-held.

While exerting a substantially consistent force of the desired magnitude on the rock specimen, the user laterally moves roller indenter 10 along the rock specimen to create an elongated trough 54 in the specimen with indenter wheel 14. Preferably, trough 54 is at least about 1 inch in length, more preferably between about 1 to about 2 inches in length, and most preferably between about 1 to about 1.5 inches in length. Wheel 14 rotates about axis 42 thereby cutting film 52 during formation of the elongated trough 54. Flexible mat layer 55 generally follows the contour of trough 54 and serves as a contour mapper of trough 54. The angle between the sidewalls of trough 54 is approximately the same as the taper angle of circumferential edge 44 of indenter wheel 14. As wheel 14 rotates, wheel edge 44 contacts dye pad 25 thereby transferring a visible marking substance to edge 44. The visible marking substance is preferably a flowable ink, dye, or gel, however, any comparable material capable of being applied to wheel edge 44 maybe used. The marking substance is transferred to the film and/or rock specimen as wheel 14 is moved along. The marking substance provides not only the visual and permanent record of the geometrical properties of trough 54, but also suppresses shear stresses from developing between indenter wheel 14 and the specimen surface. In this manner, testing of the specimen may occur without applying shear forces to the specimen to the point of specimen failure, thereby allowing the specimen to be preserved for additional testing if required.

Dye pad 25 may be changed out or refilled with marking substance from time to time as needed. To replace dye pad 25, roller indenter 10 is disassembled and pin 20 removed from casing 28. The old dye pad is then easily removed and replaced, or simply refilled, and then roller indenter 10 is reassembled. It is also within the scope of the present invention to configure indenter 10 so that dye pad 25 may be refilled without requiring complete disassembly of the indenter. Thus, the marking substance in dye pad 25 may be replenished automatically.

Next, the size of the trough is measured. In a preferred embodiment, shown in FIG. 7, an optical reader 56 is placed over the elongated trough 54 and in contact with the rock specimen 50 in order to measure the width of trough 54. Optical reader 56 comprises an magnifying glass including an eye piece 58 and a translucent bottom portion 60 for allowing light to enter the reader. The user looks through optical reader 56, and using an integrated measurement scale 61 (FIG. 8) formed therein, determines the width of trough 54. Preferably the trough presents a width of between about 0.01 to about 2 mm, more preferably between about 0.05 to about 1.5 mm, and most preferably between about 0.1 to about 1 mm.

The depth of trough 54 may also be measured and recorded. Any depth measuring device known to those of skill in the art capable of measuring the depth of trough 54 may be used. Preferably, such instrument will be portable so that it can be used in the field alongside indenter 10.

The size measurement is repeated a plurality of times over the length of trough 54 or the portion of the trough formed by the film. Preferably, the trough is measured at a minimum of three distinct places, more preferably at a minimum of five places, and most preferably at a minimum of eight places. The trough size measurements are then correlated with at least one known standard to estimate a property of the specimen. Preferably, the width measurements are averaged and compared with a database of previously analyzed specimens with known strength of values to provide an estimate of at least one property of the specimen, particularly the rock strength.

Figure 5:
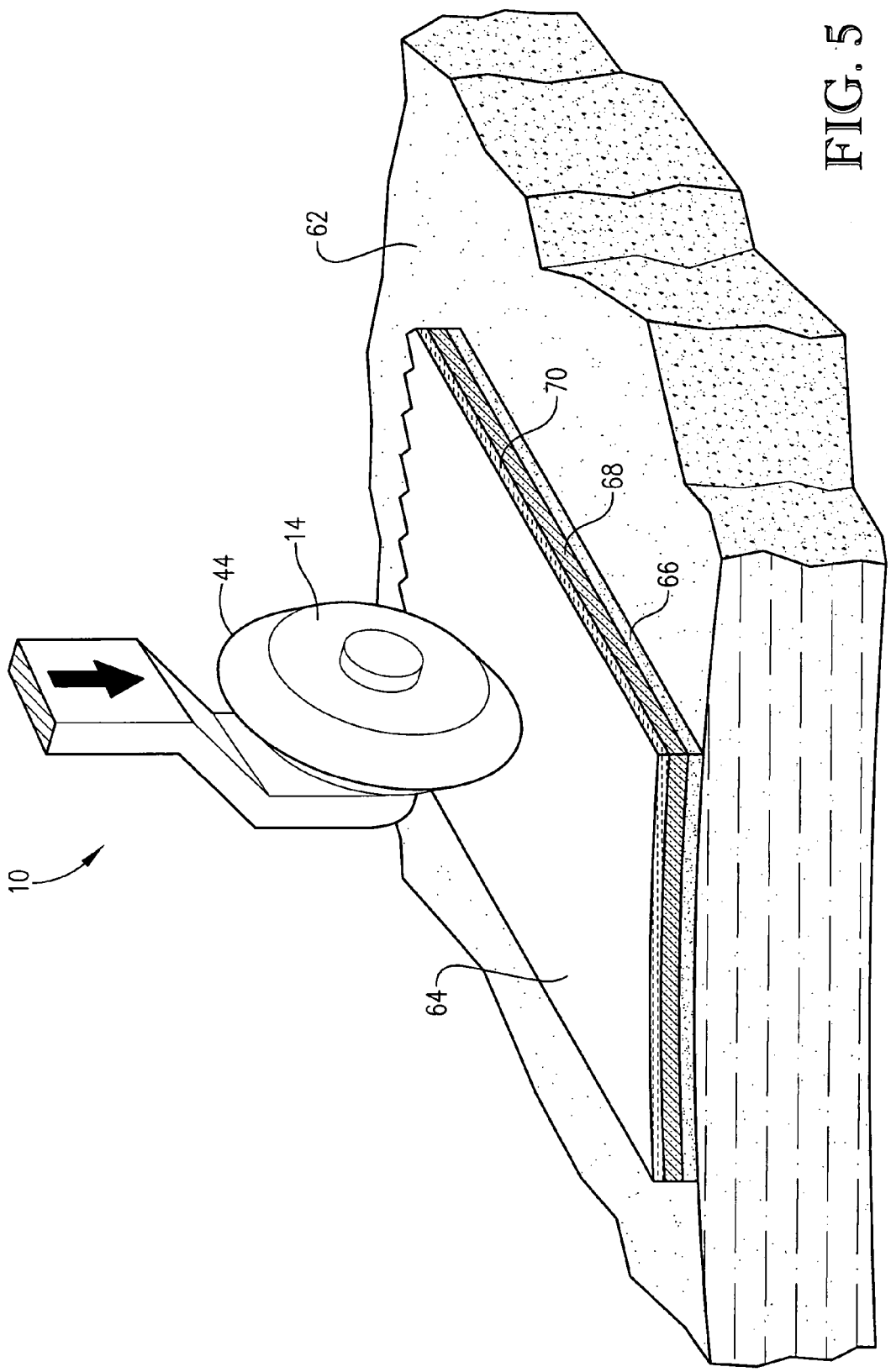
FIG. 5 is a view depicting the use of a roller indenter in conjunction with a film applied to the surface of a rock specimen.
Figure 6:
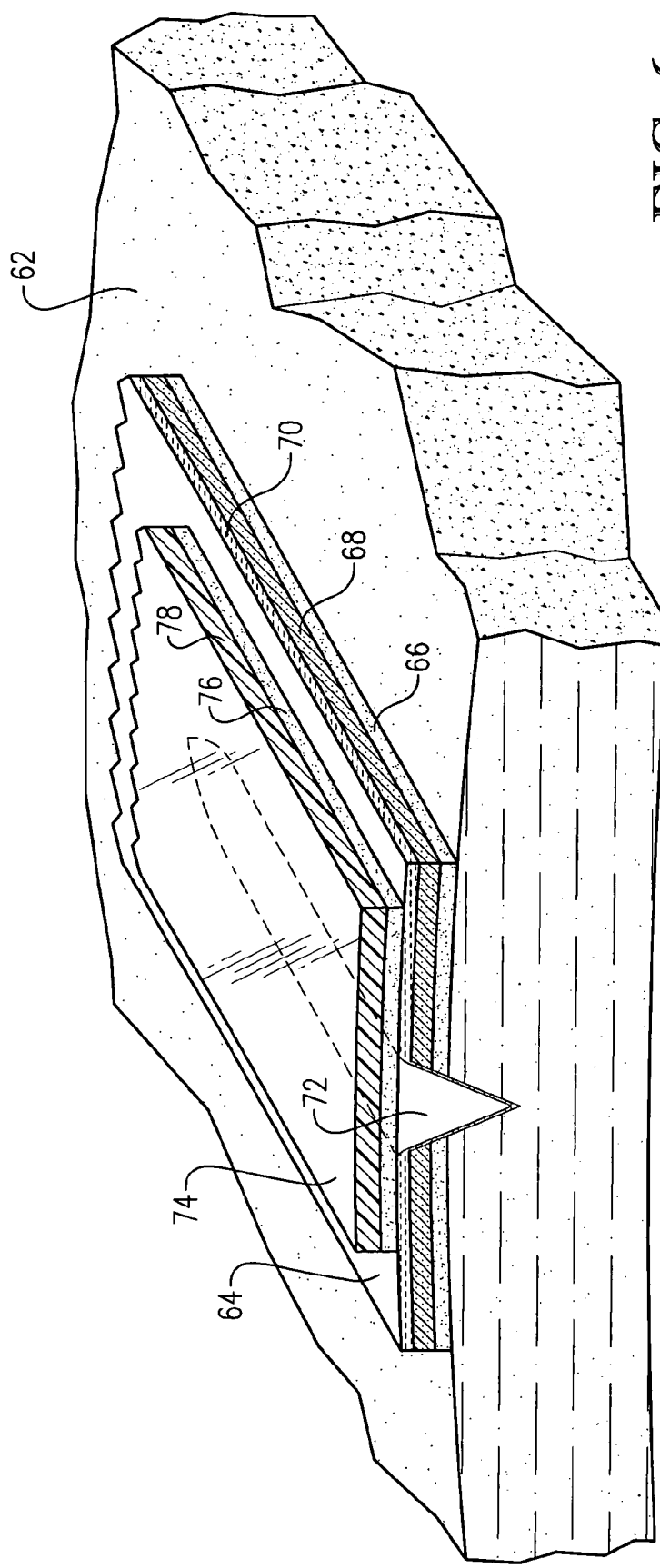
FIG. 6 is a view depicting a trough that has been formed by a roller indenter and preserved by a clear adhesive film applied over the trough.

In another embodiment, the dye pad 25 of roller indenter 10 may be removed. Instead, the dye or other marking substance may be provided as a part of the film that is initially applied to the rock specimen. Turning now to FIG. 5, a rock specimen 62 is prepared by applying a surface deformation film 64 thereto. Film 64 comprises an adhesive substrate 66, a flexible mat layer 68, and a shear suppressant gel and dye layer 70. Gel and dye layer 70 functions in a similar manner as the marking substance applied by dye pad 25 discussed above. Film 64 may be supplied as a tape, or in a roll, facilitating easy application of a desired length of film to a particular rock specimen. Film 64 generally presents a thickness of less than about 0.5 inches (12.7 mm), more preferably less than about 0.25 inches (6.35 mm), and most preferably less than about 0.1 inches (2.54 mm).

Roller indenter 10 (shown in FIG. 5 with some components removed for ease of illustration) is placed in contact with film 64. A downward force is applied to wheel 14 as roller indenter 10 is moved along rock specimen 62. Indenter wheel 14 cuts through film 6 thereby creating an elongated trough 72 in specimen 62. The marking substance in layer 70 marks the edges of trough 72 in the same manner as the marking substance that is applied directly to wheel 14 by dye pad 25. The width of trough 72 is measured in a similar fashion as shown in FIGS. 7 and 8 and the data compared with measurements from other known samples to estimate at least one property of the rock specimen, namely the rock strength.

In yet another embodiment, a pressure sensitive electronic pad may be used in place of film 64. This pad may sense changes in voltage or resistance as indenter 10 moves across the sample. These changes can be electronically recorded and correlated with known values to estimate the size (i.e., width and/or depth) of trough 72.

Trough 72 may be preserved for future analysis or measurement by application of a clear adhesive film 74 over the top of film 64. Film 74 generally comprises an adhesive layer 76 and a transparent web 78.

It is to be understood that the present invention is not merely limited to the testing of rocks. Any hard substance such as concrete, cement, synthetic resin materials, or combinations thereof may be tested using the apparatus and methods discussed herein.

The preferred forms of the invention described above are to be used as illustration only, and should not be used in a limiting sense to interpret the scope of the present invention. Obvious modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as it pertains to any apparatus not materially departing from but outside the literal scope of the invention as set forth in the following claims.

What is claimed is:

1. A method for testing the strength of a specimen, said method comprising:
    (a) using a roller indenter to create an elongated trough in at least one specimen, said roller indenter comprising a force indicator and an indenting wheel coupled to said force indicator;
    (b) measuring the size of said trough at a plurality of locations; and
    prior to step (a), applying a film to the at least one specimen,
    said film comprising a bottom adhesive substrate, a flexible mat, and a top layer including a dye.

2. The method according to claim 1, said film having a thickness of less than about 0.5 inches.

3. A method for testing the strength of a specimen, said method comprising:
    (a) using a roller indenter to create an elongated trough in at least one specimen, said roller indenter comprising a force indicator and an indenting wheel coupled to said force indicator;
    (b) measuring the size of said trough at a plurality of locations; and
    prior to step (a), applying a film to the at least one specimen,
    step (a) including cutting through said film with said roller indenter.

4. The method according to claim 3,
    step (b) being performed with a magnifying glass having an integrated optical measurement scale.

5. The method according to claim 3,
    step (b) including measuring the size of the trough at 3 or more locations.

6. The method according to claim 3; and
    (c) comparing the measurements from step (b) with a database of previously obtained measurements to provide an estimate of the strength of the at least one specimen.

7. The method according to claim 3,
    said at least one specimen comprising at least one rock specimen.

8. The method according to claim 3,
    step (b) comprising measuring the width of said trough at a plurality of locations.

9. The method according to claim 3,
    step (b) comprising measuring the depth of said trough at a plurality of locations.

10. The method according to claim 3,
    said elongated trough being at least about 1 inch in length.

11. The method according to claim 3,
    said roller indenter including an indenting wheel with a sharpened circumferential edge.

12. The method according to claim 11,
    step (a) including rolling the sharpened circumferential edge of the indenting wheel on the at least one specimen to thereby form the elongated trough.

13. The method according to claim 3,
    said elongated trough being cooperatively formed by said at least one specimen and said film.

14. The method according to claim 13,
    step (b) including measuring the width of the portion of the trough formed by the film.

15. The method according to claim 3,
    step (a) including applying a downward force of substantially constant magnitude to the at least one specimen with the roller indenter.

16. The method according to claim 15,
    said downward force having a magnitude of from about 0.5 to about 50 pounds.

17. A method for testing the strength of a specimen, said method comprising:
    (a) using a roller indenter to create an elongated trough in at least one specimen, said roller indenter comprising a force indicator and an indenting wheel coupled to said force indicator; and
    (b) measuring the size of said trough at a plurality of locations,
    said roller indenter including an indenting wheel with a sharpened circumferential edge,
    said roller indenter including a marking device for applying a visible marking substance to the circumferential edge of the indenting wheel.

18. A method for testing the strength of a specimen, said method comprising:
   (a) using a roller indenter to create an elongated trough in at least one specimen, said roller indenter comprising a force indicator and an indenting wheel coupled to said force indicator;
   (b) measuring the size of said trough at a plurality of locations; and
   (c) applying a clear adhesive film over said elongated trough thereby preserving the trough for subsequent measurement.

19. A method for testing a specimen, said method comprising:
   (a) scoring at least one specimen with a roller indenter to create an elongated trough in said at least one specimen, said roller indenter comprising a force indicator and an indenting wheel coupled to said force indicator;
   (b) measuring the size of said trough at a plurality of locations; and
   (c) correlating said size measurements with at least one known standard to estimate a property of said specimen,
   prior to step (a), applying a film to the at least one specimen comprising a bottom adhesive substrate, a flexible mat, and a top layer including a dye.

20. The method according to claim 19,
   step (a) including cutting through said film with said roller indenter.

21. The method according to claim 20,
   said elongated trough being cooperatively formed by said at least one specimen and said film,
   step (b) including measuring the width of the portion of the trough formed by the film.

22. A method for testing a specimen, said method comprising:
   (a) scoring at least one specimen with a roller indenter to create an elongated trough in said at least one specimen, said roller indenter comprising a force indicator and an indenting wheel coupled to said force indicator;
   (b) measuring the size of said trough at a plurality of locations; and
   (c) correlating said size measurements with at least one known standard to estimate a property of said specimen,
   said roller indenter including a marking device for applying a visible marking substance to the indenting wheel.

23. The method according to claim 22,
   step (c) including comparing the measurements from step (b) with a database of previously obtained measurements to provide an estimate of the strength of the at least one specimen.

24. The method according to claim 22,
   said at least one specimen comprising at least one rock specimen.

25. A roller indenter for testing the strength of a rock specimen, said indenter comprising:
   a force indicator; and
   an indenting wheel rotatably coupled to said force indicator, said indenting wheel presenting a sharpened circumferential edge,
   said force indicator including a casing having a biasing element disposed therein, and a handle slidably coupled to said casing, said handle acting to compress said biasing element when a force is applied to said handle in the same direction as the longitudinal axis of said indenter.

26. The indenter according to claim 25,
   said biasing element comprising a spring.

27. The indenter according to claim 25,
   said sharpened circumferential edge having a taper angle in the range of from about 20 to about 120 degrees.

28. The indenter according to claim 25,
   said force indicator providing an indication of the magnitude of a force imparted to the rock specimen by the indenting wheel.

29. The indenter according to claim 25,
   said force indicator being a hand-held force indicator.

30. A roller indenter for testing the strength of a rock specimen, said indenter comprising:
   a force indicator; and
   an indenting wheel rotatably coupled to said force indicator, said indenting wheel presenting a sharpened circumferential edge,
   said force indicator providing an indication of the magnitude of a force imparted to the rock specimen by the indenting wheel,
   said force indicator including a graduated casing slidably coupled with a handle, the position of said handle on said casing providing an indication of the magnitude of a force imparted to the rock specimen by the indenting wheel.

31. A roller indenter for testing the strength of a rock specimen, said indenter comprising:
   a force indicator; and
   an indenting wheel rotatably coupled to said force indicator, said indenting wheel presenting a sharpened circumferential edge,
   said indenter further comprising a marking device for applying a visible marking substance to the circumferential edge of said indenting wheel.

32. The indenter according to claim 31,
   said marking device comprising an dye pad at least a portion of which is located within said force indicator.

* * * * *